US010166022B2

United States Patent
Early et al.

(10) Patent No.: US 10,166,022 B2
(45) Date of Patent: Jan. 1, 2019

(54) METHOD AND APPARATUS FOR BONE FIXATION

(71) Applicant: Biomet C.V., Gibraltar (GI)

(72) Inventors: John Early, Dallas, TX (US); Brian Berelsman, Warsaw, IN (US); Adam Finley, Winona Lake, IN (US); Paul D'Antonio, Winona Lake, IN (US); Kevin Stone, Winona Lake, IN (US)

(73) Assignee: Biomet C.V., Warsaw, IN (US)

( * ) Notice: Subject to any disclaimer, the term of this patent is extended or adjusted under 35 U.S.C. 154(b) by 375 days.

(21) Appl. No.: 14/499,667

(22) Filed: Sep. 29, 2014

(65) Prior Publication Data

US 2016/0089138 A1    Mar. 31, 2016

(51) Int. Cl.
   *A61B 17/064* (2006.01)
   *A61B 17/00* (2006.01)
   *A61F 2/42* (2006.01)

(52) U.S. Cl.
   CPC ...... *A61B 17/0642* (2013.01); *A61B 2017/00884* (2013.01); *A61B 2017/00933* (2013.01); *A61F 2002/422* (2013.01)

(58) Field of Classification Search
   CPC .... A61B 2017/0641; A61B 17/0642–17/0646; A61B 17/0649; A61B 2017/00844; A61B 2017/00933
   USPC ............................ 606/75; 227/902
   See application file for complete search history.

(56) References Cited

U.S. PATENT DOCUMENTS

| | | | | |
|---|---|---|---|---|
| 4,454,875 A | * | 6/1984 | Pratt | F16B 15/02 606/219 |
| 4,570,623 A | * | 2/1986 | Ellison | A61B 17/0642 606/75 |
| 5,454,814 A | * | 10/1995 | Comte | A61B 17/0642 606/219 |
| 6,017,346 A | * | 1/2000 | Grotz | A61B 17/0642 606/232 |
| 2004/0092937 A1 | * | 5/2004 | Criscuolo | A61B 17/122 606/232 |

(Continued)

OTHER PUBLICATIONS

K. R. Wheeler, M.T. Karagianes, and K.R. Sump. "Porous Titanium Alloy for Prosthesis Attachment." in: Titanium Alloys in Surgical Implants (Philadelphia, ASTM, 1983), pp. 241-254.*

*Primary Examiner* — Zade Coley
*Assistant Examiner* — Jessica Weiss
(74) *Attorney, Agent, or Firm* — Schwegman Lundberg & Woessner, P.A.

(57) ABSTRACT

An implant can include a bridge member having an upper surface, a lower surface and opposed sides extending between the upper and lower surfaces, where at least the sides can be formed of a porous metal construct having a porous metal outer surface. First and second fixation members can be integrally connected with the bridge member and can include a body having a width greater than a corresponding width of the bridge member and a length greater than a corresponding length of the bridge member, where at least the body can be formed of the porous metal construct with the porous metal outer surface. The implant can be positioned into the bone segments such that the bridge member can fix the bone segments in a first direction perpendicular to the bridge member and the fixation members can fix the bone segments in a second direction parallel to the bridge member.

19 Claims, 4 Drawing Sheets

(56) References Cited

U.S. PATENT DOCUMENTS

| | | |
|---|---|---|
| 2006/0036251 A1 | 2/2006 | Reiley |
| 2006/0036322 A1 | 2/2006 | Reiley |
| 2007/0093839 A1* | 4/2007 | Beckendorf ....... A61B 17/0642 606/75 |
| 2007/0156241 A1* | 7/2007 | Reiley ................ A61B 17/1615 623/17.11 |
| 2008/0065212 A1 | 3/2008 | Zucherman et al. |
| 2008/0154316 A1 | 6/2008 | Reiley |
| 2009/0062800 A1* | 3/2009 | Shano ................ A61B 17/0642 606/75 |
| 2009/0259261 A1 | 10/2009 | Reiley |
| 2010/0292738 A1 | 11/2010 | Reiley |
| 2011/0087296 A1 | 4/2011 | Reiley et al. |
| 2011/0118796 A1 | 5/2011 | Reiley et al. |
| 2012/0022535 A1* | 1/2012 | Mayer ................ A61B 17/1682 606/75 |
| 2013/0267956 A1* | 10/2013 | Terrill ................ A61B 17/0642 606/75 |

\* cited by examiner

METHOD AND APPARATUS FOR BONE FIXATION

FIELD

The present disclosure relates generally to orthopedic surgical devices and techniques and, more particularly, to fixation devices and techniques for correction, repair, reconstruction and/or fixation/fusion of bone segments.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Surgical or medical procedures are often performed on a body, for example, a human body or anatomy, to repair, reconstruct and/or replace various portions thereof. For example, after trauma, there may be a need to fix bone segments together to immobilize the segments and permit healing. There may also be a need for fusion of bone segments or reconstruction of a bone or bone segments in connection with an osteotomy. Conventional implants that can be utilized in connection with such procedures do not provide optimal surfaces for bone in-growth and/or require separate, additional fixation systems, which require additional surgical instruments and procedures. Accordingly, there remains a need for improvement in the relevant art.

SUMMARY

This section provides a general summary of the disclosure, and is not a comprehensive disclosure of its full scope or all of its features.

In one aspect, an orthopedic implant for use in fixation or fusion of bone segments is provided in accordance with various aspects of the present disclosure. In an exemplary implementation, the orthopedic implant can include a longitudinally extending bridge member and first and second fixation members. The longitudinally extending bridge member can have an upper surface portion, an opposed lower surface portion and opposed sides extending between the upper and lower surface portions. In one exemplary implementation, at least the opposed sides can be formed of a porous metal construct having a porous metal outer surface. The first and second fixation members can be integrally connected with the bridge member at opposed longitudinal ends of the bridge member. The first and second fixation members can include a body having a body width in a direction perpendicular to a longitudinal axis of the bridge member greater than a corresponding bridge width of the bridge member. The fixation members can also include a member length between a top surface portion and an opposed bottom surface portion greater than a corresponding bridge length of the bridge member from the upper surface portion to the lower surface portion. In one exemplary implementation, at least the body can be formed of the porous metal construct and can have the porous metal outer surface. The implant can be adapted to be positioned into the bone segments such that the bridge member is adapted to fix the bone segments in a first direction perpendicular to the longitudinal axis and the fixation members are adapted to fix the bone segments in a second direction parallel to the longitudinal axis.

In another aspect, a method for fixation or fusion of bone segments is provided in accordance with various aspects of the present disclosure. In an exemplary implementation, the method can include forming a first cavity portion in a first bone segment and a second bone segment across a joint or fracture between the first and second bone segments. Second and third cavity portions can be formed in the respective first and second bone segments and in communication with the first cavity portion. A longitudinally extending implant having a porous metal construct can be inserted transversely across the joint or fracture. The longitudinally extending implant can include a first longitudinally extending bridge member and second and third fixation members integrally formed at opposed ends of the first bridge member and extending transverse to a longitudinal axis of the bridge member. The fixation members can include a larger longitudinal length from a top surface to a bottom surface thereof than a corresponding length from an upper surface to a lower surface of the bridge member. The first bridge member can be positioned in the first cavity and the second and third fixation members can be positioned in the respective second and third cavity portions. With the insertion of the implant, the first and second bone segments can be fixed in a first direction parallel to the longitudinal axis via the fixation members and in a second direction transverse to the first direction via the bridge member.

Further areas of applicability of the present disclosure will become apparent from the description provided hereinafter. The description and specific examples in this summary are intended for purposes of illustration only and are not intended to limit the scope of the present disclosure.

DRAWINGS

The present teachings will become more fully understood from the detailed description, the appended claims and the following drawings. The drawings are for illustrative purposes only and are not intended to limit the scope of the present disclosure.

Figure 1:
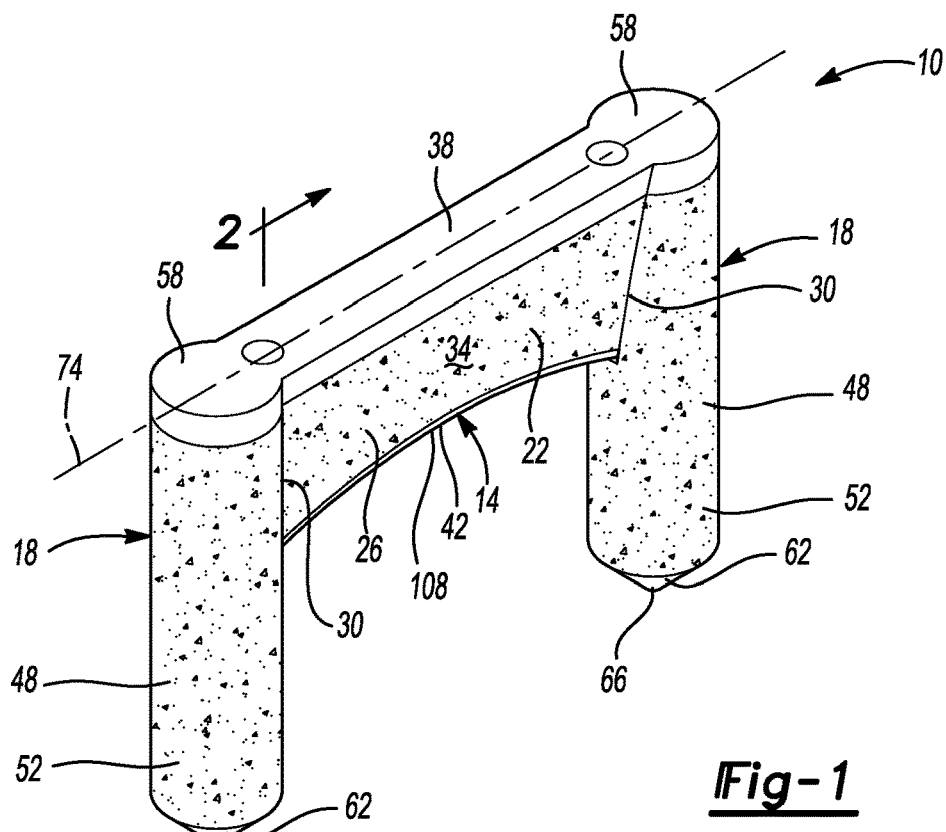
FIG. 1 is a perspective view of an exemplary bone fixation device in accordance with various aspects of the present disclosure.
Figure 4:
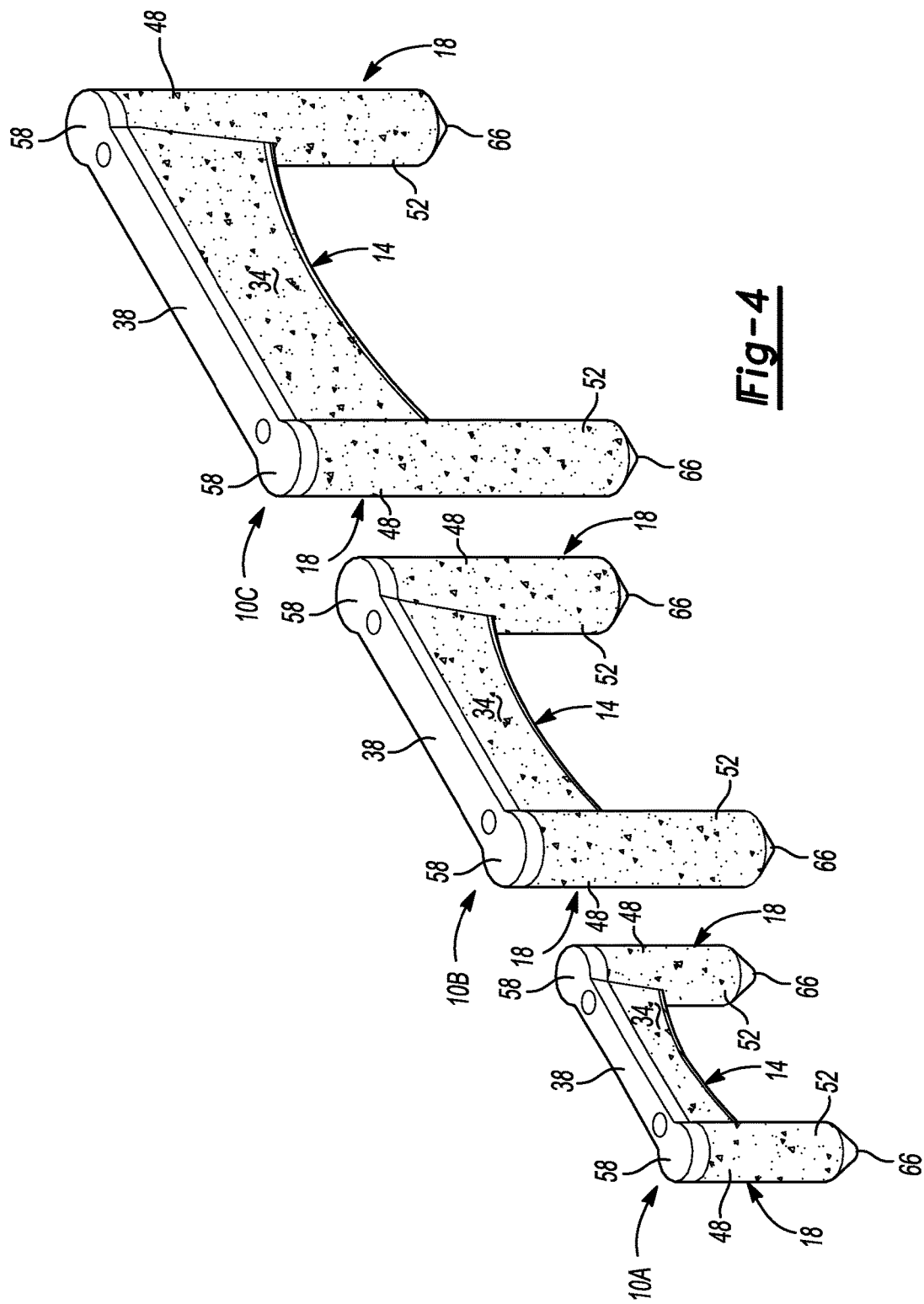
Figure 5:
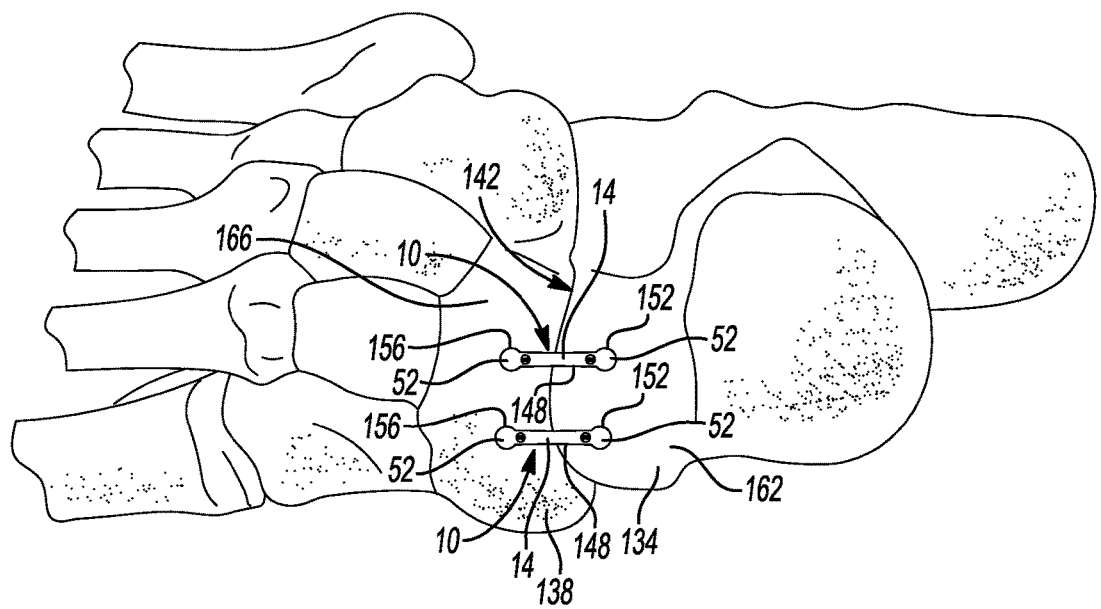
Figure 6:
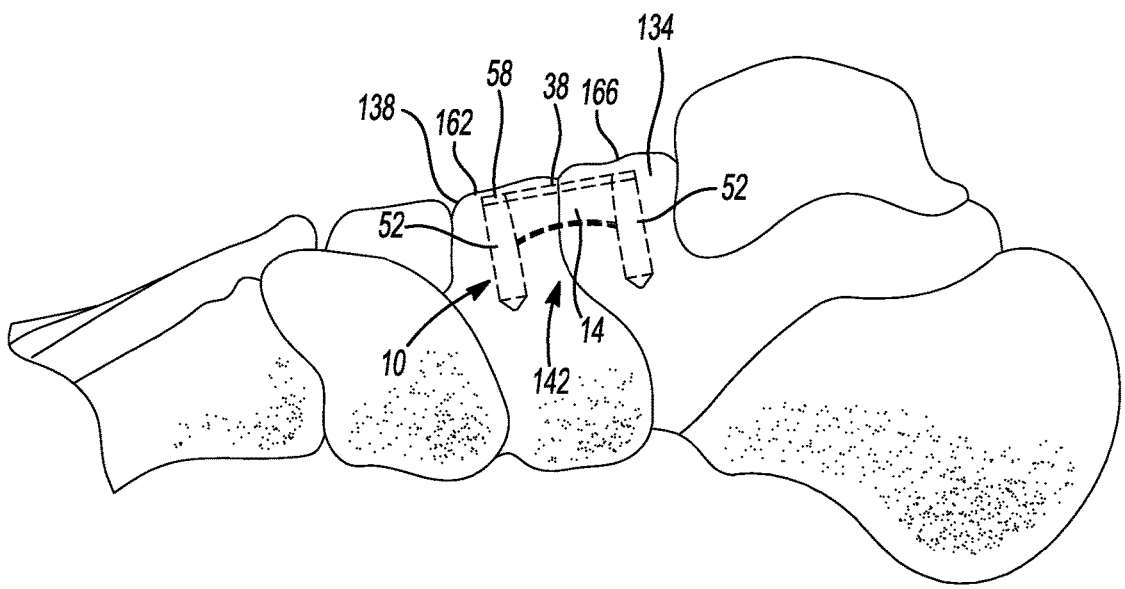

FIG. 4 is a perspective view of exemplary sizes of the bone fixation device of FIG. 1 for optional inclusion in an exemplary kit in accordance with various aspects of the present disclosure; and FIGS. 5-6 are views of an exemplary surgical technique illustrating the bone fixation device of FIG. 1 implanted relative to a Talo-Navicular joint in accordance with various aspects of the present disclosure.

DETAILED DESCRIPTION

The following description is merely exemplary in nature and is not intended to limit the present disclosure, its application, or uses. Although the following description is related generally to methods and apparatus for bone fixation in a foot, it will be appreciated that the methods and apparatus discussed herein can be applicable to various bones and/or joints of the anatomy and can be utilized in various fixation procedures or techniques.

Exemplary embodiments are provided so that this disclosure will be thorough, and will fully convey the scope to those who are skilled in the art. Numerous specific details are set forth such as examples of specific components, devices, systems and/or methods, to provide a thorough understanding of exemplary embodiments of the present disclosure. It will be apparent to those skilled in the art that specific details need not be employed, that exemplary embodiments may be embodied in many different forms and that neither should be construed to limit the scope of the disclosure. In some exemplary embodiments, well-known processes, well-known device structures, and well-known technologies are not described in detail.

The present teachings provide bone fixation devices and methods for using the same to facilitate bone fixation and healing. In an exemplary aspect, the bone fixation devices can be utilized for fracture fixation, fusion of two adjacent bone segments (e.g., joint fusion), and/or for stabilization/reconstruction of a bone or bone segments, including in connection with an osteotomy or the like. In this regard, for the sake of brevity, the devices discussed herein will be referred to as fixation devices and it will be understood that such fixation devices can perform a stabilization function as well as a fixation function between bone segments, a fusion function between bone segments and/or reconstruction of a bone or bone segments. As used herein, "bone segments" can refer to two segments of the same bone (e.g., relative to a fracture line or osteotomy) or adjacent bones (e.g., of a joint). Further, while the discussion will continue with reference to fixation of the Talo-Navicular joint, it will again be appreciated that the fixation devices discussion herein can be utilized for fixation, fusion and/or reconstruction/repair of various different small bones and/or joints, such as in the hand or foot.

With initial reference to FIGS. 1-4, an exemplary bone fixation device according to various aspects of the present teachings is shown and generally identified at reference numeral 10. As will be discussed in greater detail below, the bone fixation device 10 can, in one exemplary implementation, provide for stabilization of bone segments, such as the Talus and Navicular bones of the Talo-Navicular joint, as well as fixation of the bones with a single, unitary structure. In one exemplary aspect, the bone fixation device 10 can include a pair of fixation members in spaced relation to each other that are integrally formed with and connected by a central bridge member. As will also be discussed in greater detail below, the bone fixation device 10 can include a porous metal portion or region and can also be provided in the form of a kit including various different sizes and/or configurations of the bone fixation device 10 with or without associated instrumentation.

In the example illustrated, the bone fixation device 10 can include bridge member 14 and a fixation arrangement 18 constructed as a unitary device, as can be seen for example in FIG. 1. In one exemplary implementation, the bridge member 14 can be provided in the form of a wedge shaped structure 22 integrally formed with the fixation arrangement 18 such that the bone fixation device 10 includes a general configuration similar to a staple. As will also be discussed in greater detail below, the bone fixation device 10 can be provided in the form of a kit that includes various different sizes and/or configurations of the bridge member 14 and/or fixation arrangement 18.

The wedge structure 22 can include a longitudinally extending body 26 extending between and forming opposed longitudinal ends 30, as well as opposed sides 34, an upper or top surface portion 38 and an opposed lower or bottom surface portion 42. The wedge structure 22 can be formed of a biocompatible alloy, such as a titanium alloy. In one exemplary implementation, the bone fixation device 10 can be formed using an additive manufacturing process with a titanium alloy core and a porous metal titanium alloy construct and porous metal outer surface for the bridge member 14. For example, the opposed sides 34 and bottom surface 42 of the wedge shaped structure 22 can be formed as a porous metal construct or structure. In another exemplary implementation, the top surface portion 38 and bottom surface portion 42 can be formed of solid or substantially solid titanium alloy having a smooth or substantially smooth outer surface, as shown for example in FIG. 1. In this example, the leading edge or surface of the bone fixation device 10, namely the bottom surface 42, can be formed from the solid metal alloy with a smooth outer surface to aid with insertion into bone.

In this exemplary implementation, the porous metal structure can be a formed from a titanium alloy using an additive manufacturing process, such as with OsseoTi™, which is commercially available from Biomet Manufacturing, LLC (Warsaw, Ind., USA). Briefly, however, OsseoTi is highly biocompatible, has high corrosion resistance and includes a highly interconnected porous architecture that mimics the porous structure of human cancellous bone, which can enhance bone integration and in-growth. In one exemplary implementation, the OsseoTi porous metal construct can include a porosity of 70%.

In the exemplary implementation illustrated in FIGS. 1-4, the fixation arrangement 18 can include a pair of fixation members 48. In one implementation, the fixation members 48 can be integrally formed with the bridge member 14 to form the unitary bone fixation device 10. In one exemplary implementation, the fixation members 48 can be provided in the form of cylindrical dowel members 52 integrally formed with the bridge member 14. The dowel members 52 can include a circular or substantially circular shape in cross section and can include a top surface portion 58 and an opposed bottom surface portion 62. In the exemplary implementation illustrated, the top surface portion 58 can be formed as a solid or substantially solid structure similar to the top surface portion 38 of the bridge member 14. In this regard, the top surface portions 38 and 58 can be the same continuous portion extending over the bridge member 14 and dowel members 52, as shown for example in FIG. 1. The bottom surface portion 62 can include or define a distal tip 66 to aid with insertion into bone. Similar to the top surface portion 58, the bottom surface portion 62 can be formed as a solid or substantially solid structure with a smooth or substantially smooth outer surface, as also shown in FIG. 1 with reference to FIG. 2.

The wedge shaped structure 22 can include tapered sides 34 that are angled outwardly in a direction perpendicular or transverse to a longitudinal axis 74 of the bridge member 14 so as to form the wedge shape of the wedge shaped structure 22. In other words, a thickness 78 at the bottom surface portion 42 of the wedge shaped structure 22 can be less than a thickness 82 at the top surface portion 58, as shown for example in FIG. 2.

The dowel members 52 can include a width or diameter 92 larger than the largest width or thickness of the wedge shaped structure 22 (i.e., thickness 82) so as to provide a fixation function, as will also be discussed in greater detail below. In addition, the dowel members 52 can include a length 96 from the top surface portion 58 to the bottom surface portion 62 that is greater than a corresponding length 102 from the top surface portion 38 to the bottom surface portion 42 of the bridge member 14, as shown for example in FIGS. 1 and 2. In the exemplary configuration illustrated, the bridge member length 102 can be approximately half of the dowel member length 96 so as to provide stabilization and fixation while reducing or minimizing bone disruption or loss and insertion efforts with associated insertion techniques. In one exemplary aspect, the bottom surface 42 of the wedge shaped structure 22 can include an arcuate shape 108 along the longitudinal axis 74 such that the length 102 is greater at ends 30 of bridge member 14 than at a central point therebetween, as also shown for example in FIG. 1.

Figure 2:
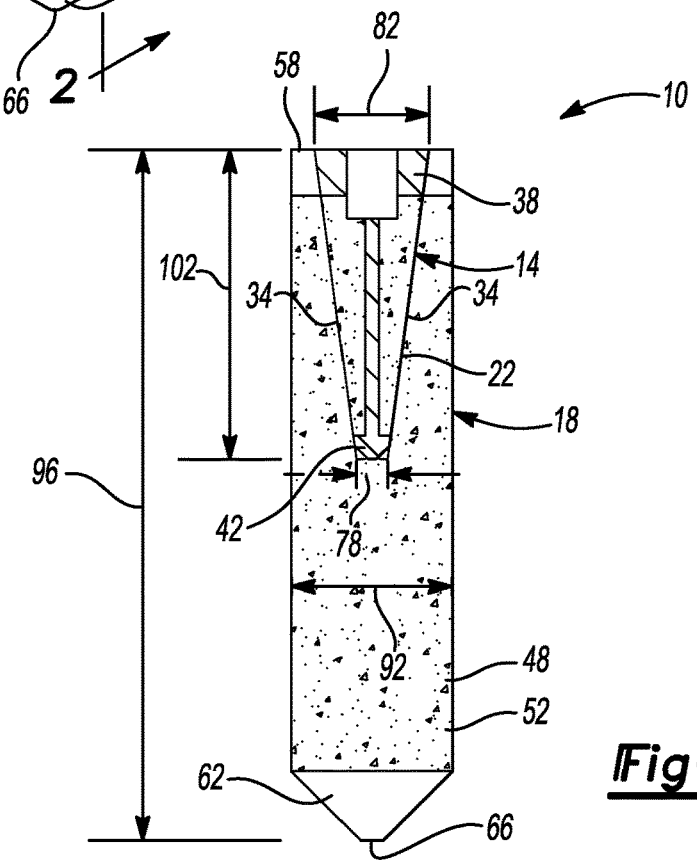
FIG. 2 is a partial sectional view of the exemplary bone fixation device of FIG. 1 in accordance with various aspects of the present disclosure.
Figure 3A:
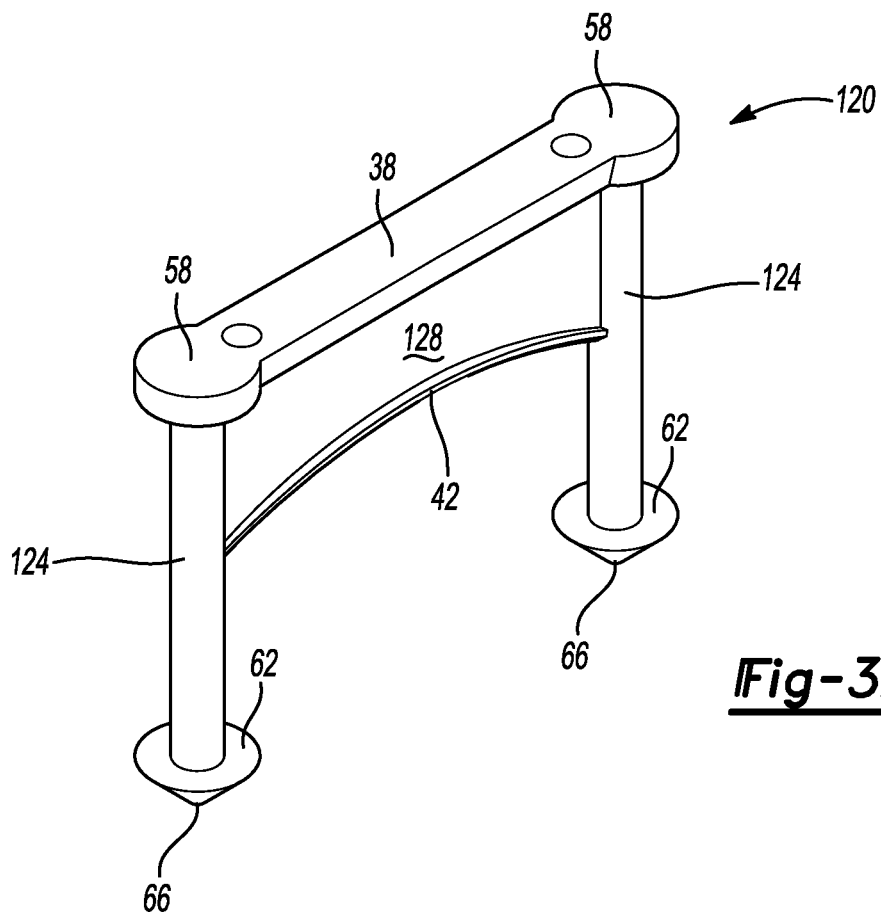
FIG. 3A is a perspective view of an exemplary core portion of the bone fixation device of FIG. 1 in accordance with various aspects of the present disclosure.
Figure 3B:
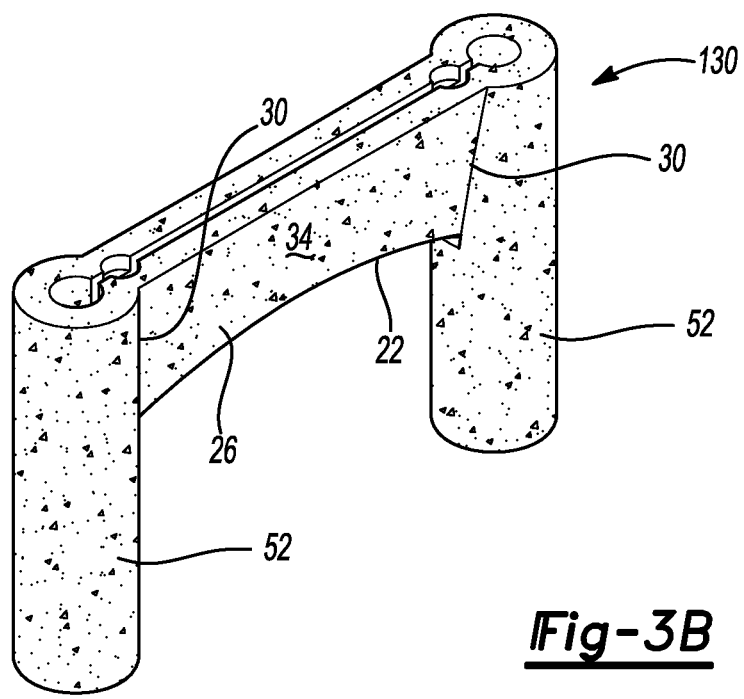
FIG. 3B is a perspective view of an exemplary porous metal portion or construct of the bone fixation device of FIG. 1 in accordance with various aspects of the present disclosure.

With particular reference to FIGS. 2-3B and continuing reference to FIGS. 1 and 4, the bone fixation device 10 can include, in one exemplary implementation, a solid or substantially solid core or support structure 120 formed with the additive manufacturing process from the same titanium alloy as the OsseoTi porous metal construct that forms the above-discussed porous metal structure and outer surfaces. In the exemplary implementation illustrated, the core 120 can include the top surfaces 38 and 58 formed as a continuous structure together with dowel cores 124 and a bridge core 128. The dowel cores 124 can extend between and are connected to the top surface 58 at one end and the bottom surface portion 62 at the opposite end. Similarly, the bridge core 128 can extend between and is connected to the top surface portion 38 at one end and the bottom surface portion 42 at the opposite end, as shown for example in FIG. 3A.

FIG. 3B illustrates the porous metal construct 130 that surrounds the core 120 except for, in the examples illustrated, the top surface portions 38, 58 and the bottom surface portions 42, 62. FIG. 2 is a sectional view of the bridge member 14 illustrating the porous metal construct 130 relative to the core structure 120. It will be appreciated, however, that the bone fixation device 10 can also be formed entirely as a porous metal construct 130 without core 120 or with only portions of the unitary device 10 (e.g., the bridge member 14 or the dowel members 52) formed entirely as a porous metal construct.

Turning now to FIG. 4 and with continuing reference back to FIGS. 1-3B, the bone fixation device 10 can be provided in various different sizes, such as sizes 10A, 10B and 10C. These different sizes can maintain the same proportions of the various portions of the bone fixation device 10 (as shown in FIG. 4) or can vary the size of only certain features, such as the length 96 of the dowel members or the thickness of the bridge member and the dowel members to accommodate various fixation procedures and/or multiple anatomies. Such different size bone fixation devices can be provided as a kit with or without associated instrumentation.

As briefly discussed above, the bone fixation device 10 can be utilized in various surgical techniques, such as for fracture fixation, fixation of two adjacent bone segments (e.g., joint fusion), and/or for stabilization/reconstruction of a bone or bone segments, including in connection with an osteotomy or the like. With additional reference to FIGS. 5 and 6 and continuing reference back to FIGS. 1-4, use of the bone fixation device 10 in an exemplary fixation technique of two bone segments will now be discussed in greater detail. In this example, the bone fixation device 10 is used for fixation of the Talus and Navicular bones 134, 138 that form the Talo-Navicular joint 142, as shown in FIGS. 5 and 6.

The bone segments the Talus and Navicular bones 134, 138) can be prepped for implantation of the bone fixation device 10. A high speed burr or other suitable bone cutting or removal device can remove a portion of bone from the Talus bone 134 and Navicular bone 138 to create a pocket or cavity 148 for receipt of the bridge member 14. A hole 152 in the Talus bone 134 and another hole 156 in the Navicular bone 138 can also be created for receipt of the dowel members 52. In one exemplary aspect, the cavity 148 can be formed perpendicular or substantially perpendicular to an axis or line of the joint 142 such that the bone fixation device 10 can be implanted perpendicular or substantially perpendicular to the joint 142. In one exemplary aspect, the joint and/or bone segments (such as with fracture fixation), can be compressed prior to forming the cavity/holes 148, 152 and 156.

With the bones 134, 138 prepared, the bone fixation device 10 can be inserted such that the bridge member 14 is received in the cavity 148 and the dowel members 52 are received in the holes 152, 156. In the examples illustrated, the dowel members 52 can be received in the holes 152, 156 prior to the bridge member 14 being received in the cavity 148. In one exemplary aspect, the holes 152, 156 can include a diameter slightly smaller than a diameter of the dowel members 52 such that an impactor can be utilized to drive the bone fixation device 10 into the Talus and Navicular bones 134, 138. In one exemplary technique, the bone fixation device 10 can be inserted into the Talus and Navicular bones 134, 138 such that the top surfaces 38, 58 are flush with or slightly below outer surfaces 162, 166 of the respective Talus and Navicular bones 134, 138, as shown for example in FIGS. 5 and 6. As can be seen in FIGS. 5 and 6, one or more bone fixation devices 10 can be inserted relative to or across the Talo-Navicular joint 142 for stabilization and fixation of the joint. Once implanted, bridge member 14 of the bone fixation device 10 can be positioned perpendicular or substantially perpendicular to the joint 142. The bridge member 14 can also span the joint 142 and be in contact or engagement with both bone segments.

As discussed immediately above, the implanted bone fixation device 10 can provide for fusion of the Talo-Navicular joint 142. Once implanted, the bone fixation device 10 can substantially prevent or eliminate distraction of the bone segments (e.g., Talus and Navicular bones 134, 138) forming the joint 142 through use of the dowel members 52 positioned in each bone segment (i.e., Talus and Navicular bones 134, 138), as well as substantially prevent or eliminate side-side motion or micro-motion of the bones forming joint 142 through use of the bridge member 14 engaging both bone segments (i.e., Talus and Navicular bones 134, 138). More particularly, in the example technique illustrated, the dowel members 52 can prevent anterior-posterior distraction of the Talus and Navicular bones 134, 138 and the bridge member 14, with its length 102, can prevent medial-lateral relative shifting and/or micro-motion of the Talus and Navicular bones 134, 138.

The bone fixation device 10 thus provides for stabilization and fixation/fusion of the Talo-Navicular joint 142 (or two bone segments) with a single device. Through use of this single device, the associated surgical technique reduces surgical steps (e.g., one insertion step for stabilization/fixation), reduces the number of implants required and thus the complexity of the operating room preparation and associated procedure, as well as reduces the time required to perform the technique. In addition, the porous metal structure of the bone fixation device 10 can provide for enhanced bone in-growth and accelerated healing.

While one or more specific examples or aspects have been described and illustrated, it will be understood by those skilled in the art that various changes may be made and equivalence may be substituted for elements thereof without departing from the scope of the present teachings as defined in the claims. Furthermore, the mixing and matching of features, elements and/or functions between various examples may be expressly contemplated herein so that one skilled in the art would appreciate from the present teachings that features, elements and/or functions of one example may be incorporated into another example as appropriate, unless described otherwise above. Moreover, many modifications may be made to adapt a particular situation or material to the present teachings without departing from the essential scope thereof.

The terminology used herein is for the purpose of describing particular example implementations only and is not intended to be limiting. As used herein, the singular forms "a," "an," and "the" may be intended to include the plural forms as well, unless the context clearly indicates otherwise. The term "and/or" includes any and all combinations of one or more of the associated listed items. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

What is claimed is:

1. An orthopedic implant for use in fixation or fusion of bone segments, the implant comprising:
   a longitudinally extending bridge member having an upper surface portion, an opposed lower surface portion and opposed sides extending between the upper and lower surface portions, at least the opposed sides being formed of a porous metal construct having a porous metal outer surface, wherein the opposed sides of the bridge member taper outwardly all the way from the lower surface portion up to the upper surface portion such that the bridge member includes a wedge shaped structure with the lower surface portion having a smaller width than a corresponding width of the upper surface portion; and
   first and second cylindrical fixation members integrally connected with the bridge member at opposed longitudinal ends of the bridge member, the first and second fixation members including a cylindrical body having a body width in a direction perpendicular to a longitudinal axis of the bridge member greater than a corresponding bridge width of the bridge member and a member length between a top surface portion and an opposed bottom surface portion greater than a corresponding bridge length of the bridge member from the upper surface portion to the lower surface portion, at least the body being formed of the porous metal construct and having the porous metal outer surface;
   wherein the bridge member and the first and second cylindrical fixation members include a solid core structure including a bridge core and integrally connected first and second cylindrical fixation member cores and the solid core structure is at least partially covered by the porous metal outer surface and wherein the lower surface portion of the bridge member is an exposed surface of the bridge core and is not covered by the porous metal;
   wherein the implant is adapted to be positioned into the bone segments such that the bridge member is adapted to fix the bone segments in a first direction perpendicular to the longitudinal axis and the fixation members are adapted to fix the bone segments in a second direction parallel to the longitudinal axis.

2. The implant of claim 1, wherein the bridge member is sized and constructed such that the lower surface portion and opposed sides proximate thereto include a single arcuate configuration extending from the first fixation member to the second fixation member such that the bridge length is longer proximate the fixation members and shorter at a central distance therebetween.

3. The implant of claim 1, wherein the bridge member is sized and constructed such that the lower surface portion and opposed sides proximate thereto include an arcuate configuration such that the bridge length is longer proximate the fixation members and shorter at a central distance therebetween.

4. The implant of claim 3, wherein the bridge length is approximately half of the member length of the first and second fixation members.

5. The implant of claim 1, wherein the upper surface portion and the lower surface portion are formed as solid structure portions of the bridge member having a substantially smooth outer surface, and wherein the lower surface portion includes a blunt, non-sharpened surface.

6. The implant of claim 5, wherein the top surface portion and the bottom surface portion of the first and second fixation members are formed as solid structure portions of the bridge member having a substantially smooth outer surface.

7. The implant of claim 6, wherein the upper surface portion and the top surface portion together form a continuous and flush upper surface of the implant.

8. The implant of claim 1, wherein the first and second fixation members comprise first and second dowel members having a cylindrical configuration.

9. The implant of claim 8, wherein the bottom surface portion of the first and second dowel members is formed as a solid structure having a substantially smooth outer surface.

10. The implant of claim 9, wherein the bottom surface portion is sized and shaped to form a distal tip.

11. The implant of claim 1, wherein the first and second fixation members together with the bridge member form a unitary component formed from an additive manufacturing process.

12. A method for fixation or fusion of bone segments, the method comprising:
    forming a first cavity portion in a first bone segment and a second bone segment across a joint or fracture between the first and second bone segments;
    forming second and third cavity portions in the respective first and second bone segments and in communication with the first cavity portion;
    inserting a longitudinally extending implant having a porous metal construct transversely across the joint or fracture, the longitudinally extending implant including a first longitudinally extending bridge member, wherein the first bridge member includes a wedge shaped configuration with tapered opposing sides angled outwardly all the way from a lower surface portion up to an upper surface portion such that the bridge member includes a wedge shaped structure with the lower surface portion having a smaller width than a corresponding width of the upper surface portion, and second and third fixation members integrally formed at opposed ends of the first bridge member and extending transverse to a longitudinal axis of the first bridge member, the second and third fixation members including a larger longitudinal length from a top surface to a bottom surface thereof than a corresponding length from the upper surface portion to the lower surface portion of the first bridge member, wherein the first bridge member is positioned in the first cavity and the second and third fixation members are positioned in the respective second and third cavity portions, and wherein the bridge member and the first and second cylindrical fixation members include a solid core structure including a bridge core and integrally connected first and second cylindrical fixation member cores and the solid core structure is at least partially covered by the porous metal outer surface and wherein the lower surface portion of the bridge member is an exposed surface of the bridge core and is not covered by the porous metal; and fixing, with the insertion of the implant, the first and second bone segments in a first direction parallel to the longitudinal axis via the fixation members and in a second direction transverse to the first direction via the bridge member.

13. The method of claim 12, wherein fixing includes fixing, with the insertion of the implant and free from additional fixation devices, the first and second bone segments in a first direction parallel to the longitudinal axis via the second and third fixation members and in a second direction transverse to the first direction via the first bridge member.

14. The method of claim 12, wherein the lower surface includes an arcuate configuration spanning between the second and third fixation members so as to lower an insertion effort when the implant is inserted transversely across the joint or fracture.

15. The method of claim 12, wherein the length of the first bridge member from the upper surface to the lower surface is approximately half of the longitudinal length of the second and third fixation members thereby enabling the first bridge member to fix the first and second bone segments in the second direction upon insertion of the implant.

16. The method of claim 12, further comprising compressing the first and second bone segments in a direction toward the fracture or joint prior to forming the cavities and inserting the implant.

17. The method of claim 12, wherein inserting the longitudinally extending implant having a porous metal construct transversely across the joint includes positioning the first bridge member in the first cavity such that the first bridge member extends transversely across the fracture or joint.

18. The method of claim 17, wherein inserting the longitudinally extending implant having a porous metal construct transversely across the joint includes positioning the second and third fixation members in the second and third cavity portions before positioning the first bridge member in the first cavity portion.

19. The method of claim 18, wherein the lower surface includes an arcuate configuration spanning between the second and third fixation members so as to lower an insertion effort when the implant is inserted transversely across the joint or fracture.

* * * * *